United States Patent
Danjo et al.

(10) Patent No.: US 7,357,881 B2
(45) Date of Patent: Apr. 15, 2008

(54) CYCLOAMIDE-TRANSITION METAL COMPLEXES AND BLEACH CATALYSTS

(75) Inventors: Hiroshi Danjo, Wakayama (JP); Hiromoto Mizushima, Wakayama (JP)

(73) Assignee: Kao Corporation, Tokyo (JP)

( * ) Notice: Subject to any disclaimer, the term of this patent is extended or adjusted under 35 U.S.C. 154(b) by 501 days.

(21) Appl. No.: 10/505,165

(22) PCT Filed: Mar. 4, 2003

(86) PCT No.: PCT/JP03/02491

§ 371 (c)(1),
(2), (4) Date: Mar. 22, 2005

(87) PCT Pub. No.: WO03/074539

PCT Pub. Date: Sep. 12, 2003

(65) Prior Publication Data

US 2005/0161635 A1    Jul. 28, 2005

(30) Foreign Application Priority Data

Mar. 6, 2002    (JP) .............................. 2002-059986
Dec. 11, 2002    (JP) .............................. 2002-359665

(51) Int. Cl.
*C11D 3/39* (2006.01)
(52) U.S. Cl. .............................. 252/186.1; 252/186.33; 252/186.43; 510/311; 540/465
(58) Field of Classification Search .............. 252/186.1, 252/186.33, 186.43; 510/311; 540/465
See application file for complete search history.

(56) References Cited

U.S. PATENT DOCUMENTS

| | | | | |
|---|---|---|---|---|
| 4,686,062 A | * | 8/1987 | Kermode et al. | ............ 510/315 |
| 5,876,625 A | * | 3/1999 | Collins et al. | ......... 252/186.33 |
| 6,818,149 B2 | * | 11/2004 | Boerzel et al. | ........... 252/186.1 |

FOREIGN PATENT DOCUMENTS

| | | |
|---|---|---|
| EP | 306089 A2 * | 3/1989 |
| JP | 01-097267 | 4/1989 |
| JP | 7-65074 | 7/1995 |
| JP | 08-067687 | 3/1996 |
| JP | 11-507689 | 7/1999 |
| JP | 11-515049 | 12/1999 |
| WO | 95/34628 | 12/1995 |
| WO | 97/48710 | 12/1997 |
| WO | 98/03625 | 1/1998 |
| WO | 98/58735 | 12/1998 |
| WO | 99/64156 | 12/1999 |

OTHER PUBLICATIONS

Moody, E.W. et al. 2001, Journal of Radioanalytical and Nuclear Chemistry, vol. 248, No. 2, p. 431-437.*
Horwitz et al., J. Phys. Chem. B, 2001, vol. 105, 8821-8828.*

* cited by examiner

*Primary Examiner*—Mark Eashoo
*Assistant Examiner*—Peter Godenschwager
(74) *Attorney, Agent, or Firm*—Oblon, Spivak, McClelland, Maier & Neustadt, P.C.

(57) ABSTRACT

The invention provides a bleaching catalyst and a bleaching composition having a sufficient bleaching effect even at low temperatures and being excellent in an effect of preventing color migration in fibers with less bleach of dyes and less damage to fibers. The invention provides a cyclic amide transition metal complex (1), a bleaching catalyst containing the same, and a bleaching composition containing the bleaching catalyst and a peroxy bleaching agent selected from hydrogen peroxide and a peroxide or an organic peracid generating hydrogen peroxide in an aqueous solution.

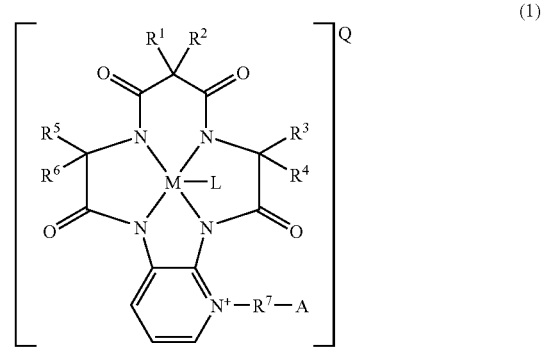

wherein $R^1$ to $R^6$ represent H, a $C_{1-16}$ hydrocarbon or perfluoroalkyl group or a halogen atom, $R^7$ represents a $C_{1-18}$ alkylene or perfluoroalkylene group, A represents a group having 1 to 3 quaternary ammonium groups substituted with an alkyl group or linked with an alkylene group, or a heterocyclic aromatic quaternary cation group, or the like, M represents a transition metal, L represents a ligand, and Q represents a counterion.

8 Claims, No Drawings

CYCLOAMIDE-TRANSITION METAL COMPLEXES AND BLEACH CATALYSTS

FIELD OF THE INVENTION

The present invention relates to a cyclic amide transition metal complex having an ability to activate bleaching and a bleaching catalyst containing the same, as well as a bleaching composition having an excellent bleaching effect even at low temperatures and being also excellent in an effect of preventing color migration in fibers with less bleach of dyes and less damage to fibers.

BACKGROUND OF THE INVENTION

Use of a peroxy bleaching agent in washing, such as hydrogen peroxide etc., belongs to known technology. This peroxy bleaching agent is used at high temperatures and can bleach stains with tea, coffee, wine, fruit etc. However, the bleaching effect of the peroxy bleaching agent is significantly lowered at 60° C. or less, and therefore, use of a transition metal complex having an ability to activate bleaching in combination with the peroxy bleaching agent has been examined; for example, JP-B 7-65074 discloses a manganese complex with cyclic polyamine as a ligand, JP-A 11-507689 discloses a cobalt ammine complex, JP-A 8-67687 and JP-A 11-515049 disclose a Schiff base derivative complex of manganese or cobalt, and WO-A 95/34628 and WO-A 97/48710 disclose an iron complex with a pyridyl methylamine derivative as a ligand. However, these complexes fail to achieve a sufficient bleaching effect on polyphenol-based stains such as stains with tea, and bring about problems such as decolorization of dyes and damage to fibers.

It is important for a factor for allowing a transition metal complex-containing bleaching composition to exhibit a bleaching activity that the complex itself is stable in the form of an aqueous bleach solution, and upon reacting with a hydrogen peroxide source, forms a certain kind of oxidized active species to react with stains. In addition, whether or not the catalyst can approach a subject of bleaching (fibers (cloth) and rigid surfaces of glass, pottery etc.) is also mentioned as another important factor. Both the subject of bleaching and a majority of stains are negatively charged (anionic), and the peroxides such as hydrogen peroxide sources are also anionic, but for preferable electrostatic interaction, it is advantageous that the catalyst itself is cationic (JP-A 1-97267). Actually, the manganese complex described in JP-B 7-65074 and the cobalt complex described in JP-A 11-507689 are designed to be cationic complexes so as to easily approach fibers (cloth). However, the bleaching compositions containing such complexes have problems such as decolorization of dyes and damage to fibers as described above.

On the other hand, a large cyclic tetramide transition metal complex described in WO-A 98/03625 is excellent in an ability to bleach a wide variety of stains with tea, wine, fruit etc. in aqueous solution, but is poor in an ability to bleach stains adhering to a cloth. An estimated reason for this insufficient ability is that this complex is anionic and thus hardly approaches a negatively charged cloth.

Further, WO-A 98/58735 discloses a compound having a pyridine skeleton, and WO-A 99/64156 discloses a compound having a pyridinium ring, but these compounds are different in structure from the compound of the present invention, and do not exhibit an excellent effect achieved by the present invention.

SUMMARY OF THE INVENTION

The present invention provides a bleaching catalyst and a bleaching composition having a sufficient bleaching effect even at low temperatures and excellent in an effect of preventing color migration in fibers with less bleach of dyes and less damage to fibers.

The present invention provides a cyclic amide transition metal complex represented by formula (1) (hereinafter referred to as cyclic amide transition metal complex (1)), a bleaching catalyst containing the same, and a bleaching composition containing (a) a bleaching catalyst containing the cyclic amide transition metal complex (1) and (b) a peroxy bleaching agent selected from hydrogen peroxide and a peroxide or an organic peracid generating hydrogen peroxide in an aqueous solution.

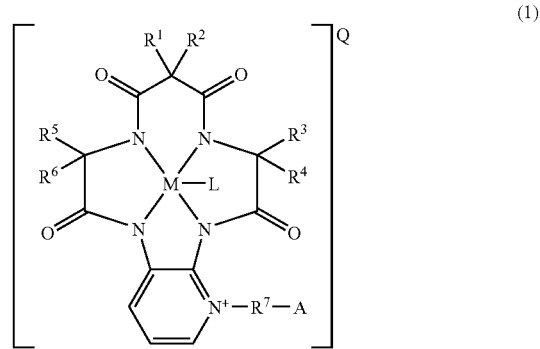

(1)

wherein $R^1$, $R^2$, $R^3$, $R^4$, $R^5$ and $R^6$ are the same or different, and each represents a hydrogen atom, a C1 to C16 hydrocarbon or perfluoroalkyl group or a halogen atom, $R^7$ represents an optionally substituted C1 to C18 alkylene or perfluoroalkylene group, A represents a group having 1 to 3 quaternary ammonium groups substituted with a linear or branched alkyl group or linked with a linear or branched alkylene group, a cyclic quaternary ammonium group, or a heterocyclic aromatic quaternary cation group which may be substituted with a linear or branched alkyl group, M represents a transition metal, L represents a ligand, and Q represents an arbitrary counterion equilibrated stoichiometrically with an electric charge of the compound.

DETAILED DESCRIPTION OF THE INVENTION

In the cyclic amide transition metal complex (1) in the present invention, the groups represented by $R^1$, $R^2$, $R^3$, $R^4$, $R^5$ and $R^6$ include a hydrogen atom, a C1 to C16 alkyl or a perfluoroalkyl group or a halogen atom such as F, Br, Cl or I, but from the viewpoint of oxidation-resisting stability and bleaching activity of the catalyst, each of the groups is preferably a methyl group, a fluorine atom or a perfluoroalkyl group, more preferably a methyl group.

$R^7$ is preferably a C1 to C18 linear or branched alkylene or perfluoroalkylene group, specifically an alkylene group such as n-ethylene group, n-propylene group, n-butylene group, n-pentylene group, n-hexylene group, n-heptylene group, n-octylene group, n-nonylene group, n-decylene group, n-undecylene group and n-dodecylene group or a perfluoroalkylene group such as n-perfluorohexylene group, more preferably a $-(CH_2)_n-$ group (n is an integer of 1 to 18), particularly preferably a C3 to C8 linear alkylene group such as n-propylene group, n-butylene group, n-pentylene group, n-hexylene group, n-heptylene group and n-octylene group.

A has the meaning defined above, wherein the group having 1 to 3 quaternary ammonium groups substituted with a linear or branched alkyl group or linked with a linear or branched alkylene group includes a quaternary ammonium group substituted with a C1 to C18 alkyl group, a group having 2 to 3 quaternary ammonium groups substituted with a C1 to C3 alkyl group and linked with a C1 to C18 alkylene group, etc. The cyclic quaternary ammonium group includes a pyrrolidinium group, piperidinium group etc. The heterocyclic aromatic quaternary cation group which may be substituted with a linear or branched alkyl group includes a pyridinium group, pyrazinium group, pyrimidinium group etc., each of which may be substituted with a C1 to C18 alkyl group. Among these groups, $-N^+(CH_3)_2(C_mH_{2m+1})$ (m is an integer of 1 to 18), $-N^+(CH_3)_2-(CH_2)_p-N^+(CH_3)_3$ (p is an integer of 1 to 18) and a pyridinium group are preferable, and a trimethyl ammonium group [$-N^+(CH_3)_3$], a dimethyl-octyl ammonium group [$-N^+(CH_3)_2(C_8H_{17})$], a dimethyl-dodecyl ammonium group [$-N^+(CH_3)_2(C_{12}H_{25})$], a dimethyl-trimethyl ammoniopropyl ammonium salt [$-N^+(CH_3)_2-(CH_2)_3N^+(CH_3)_3$] and a pyridinium group are more preferable.

M includes Mn, Fe, Co, Ni, Cu and Zn, among which Fe, Mn and Co are preferable in respect of bleaching activity, and Fe, particularly Fe(III), is preferable in respect of safety. L represents a ligand which is specifically water, a lower alcohol (methanol, ethanol etc.), a solvent molecule such as acetonitrile, a halogen atom such as Cl, Br etc., an amine molecule such as pyridine, imidazole, trimethylamine etc., or the like, among which water, a lower alcohol and Cl are preferable. Q represents an arbitrary counterion equilibrated stoichiometrically with an electric charge of the compound, and includes a counter anion such as $Cl^-$, $Br^-$, $I^-$, $NO_3^-$, $NCS^-$, $ClO_4^-$, $OH^-$ etc. when the charge of the complex as a whole is positive, or an alkali metal ion such as $Li^+$, $Na^+$, $K^+$ etc., an alkaline earth metal ion such as $Mg^{2+}$, $Ca^{2+}$ etc., a counter cation such as alkyl ammonium ion etc. when the charge of the complex as a whole is negative.

Examples of the cyclic amide transition metal complex (1) include compounds represented by the following chemical structures. In the structures, the ligand L and counterion Q are omitted.

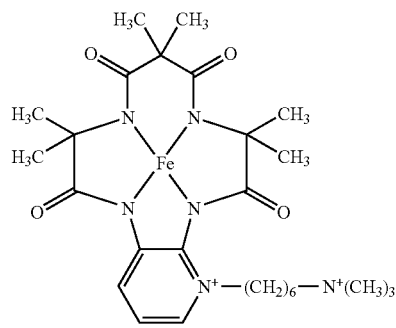

I-a

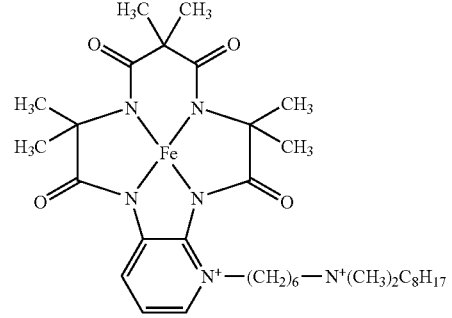

I-b

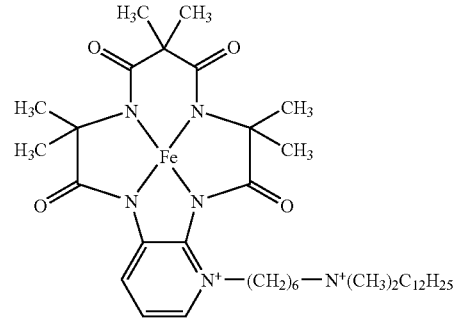

I-c

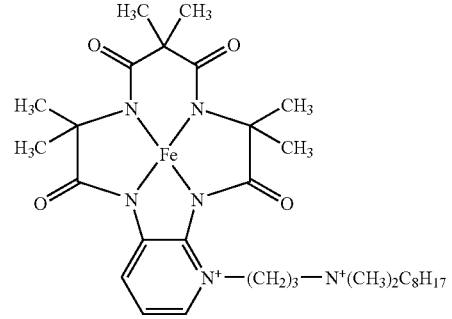

I-d

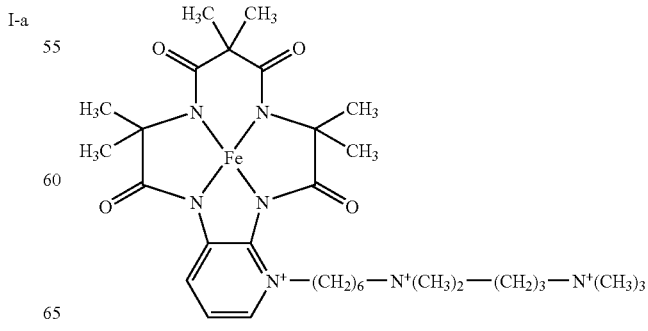

II-a

-continued

III-a
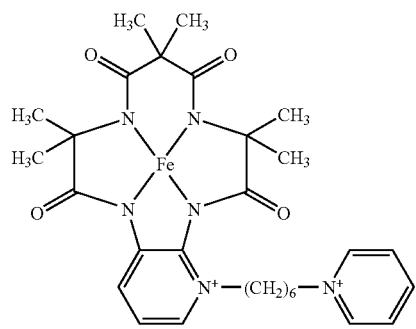

IV-a
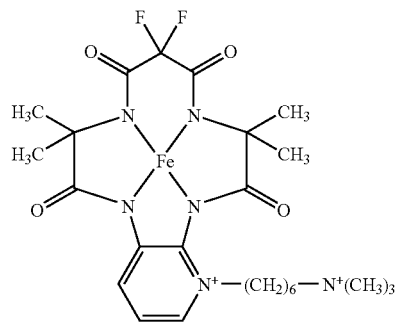

IV-b
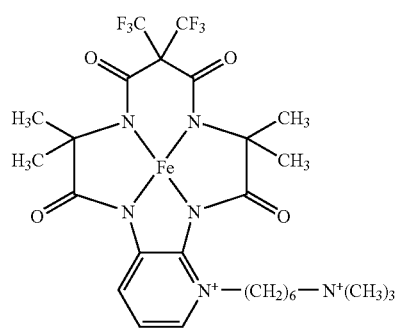

IV-c
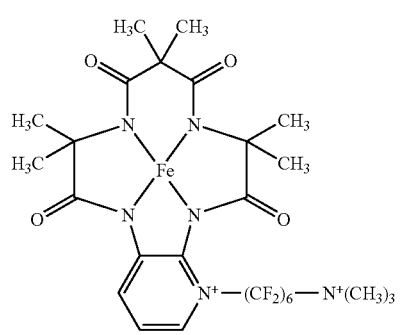

-continued

V-a
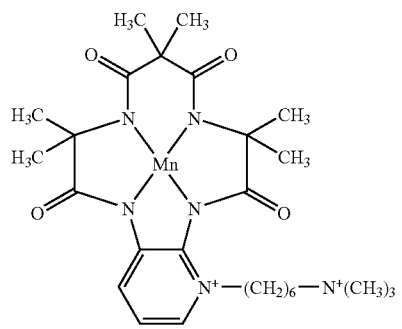

V-b
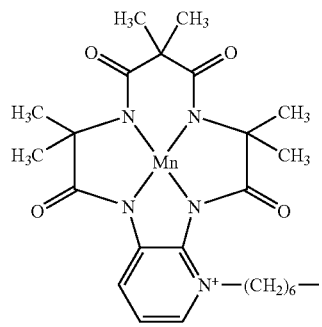

V-c
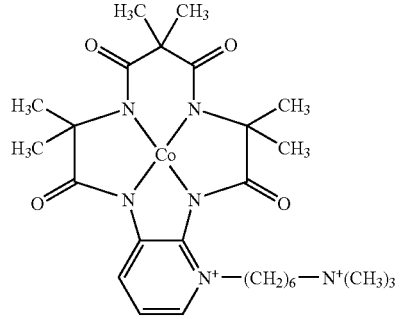

A general method of synthesizing the cyclic amide transition metal complex (1) of the present invention is shown below. For example, a Fe complex of formula (1) wherein M is Fe can be synthesized by a method shown in the following scheme 1 using a macrolinker represented by formula (2) and a heterocyclic aromatic diamine represented by formula (4) as the starting material, as described by Collins, T. J. et al. in J. Am. Chem. Soc., 120, 11540-11541 (1998), or in WO 9858735.

Scheme 1

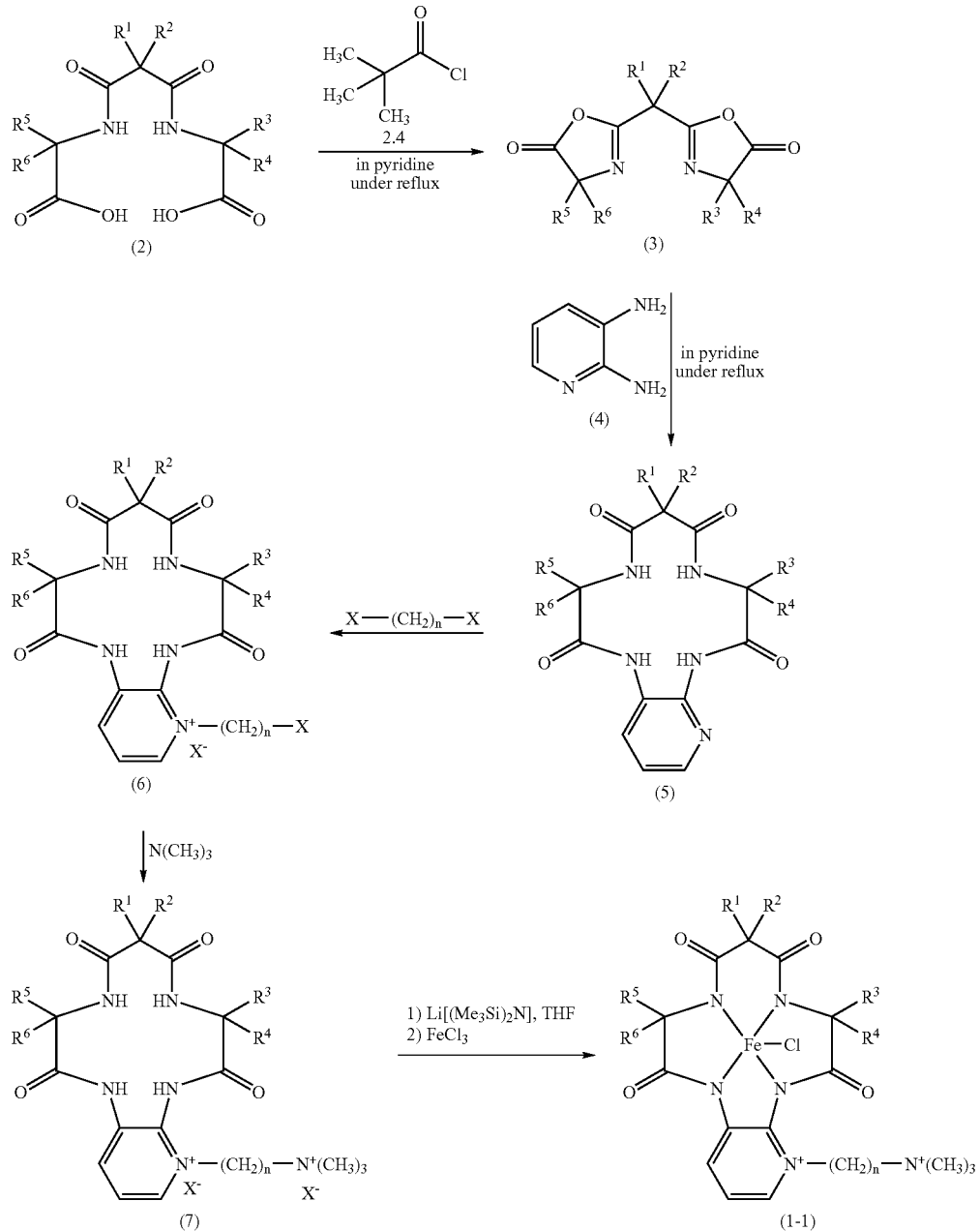

wherein $R^1$, $R^2$, $R^3$, $R^4$, $R^5$, $R^6$ and n have the same meanings as defined above, X represents a halogen atom, and Me represents a methyl group.

That is, a macrolinker represented by formula (2), obtained by coupling α-aminocarboxylic acid at about 70° C. in pyridine with malonic acid dichloride substituted at the α-position is dehydrated in pyridine (under reflux) with about 2.4 equivalents of pivaloyl chloride to form an oxazolone represented by formula (3). One equivalent of 2,3-diaminopyridine represented by formula (4) is added to close the ring, and the sample is refluxed in pyridine for 3 days to give a large cyclic tetramide represented by formula (5). The resulting large cyclic tetramide is reacted with a large excess of α,ω-dihalogenated alkyl at 100° C. for 6 days, whereby a large cyclic tetramide converted into ω-halogenoalkyl pyridinium represented by formula (6) is obtained. Then, the halogen group in this large cyclic tetramide is converted into a tertiary ammonium group by reaction, for example, with a tertiary amine such as trimethylamine, whereby a tetramide represented by formula (7) is obtained. Finally, an amide proton is eliminated from the tetramide represented by formula (7) in tetrahydrofuran (THF) with a base (about 6 equivalents) such as bis(trimethylsilyl)amide lithium to generate an amide anion. A large cycle tetraamide Fe complex modified with ω-quaternary ammonioalkyl pyridinium, represented by formula (1-1), can be obtained, for example, by adding about 1.5 equivalents of $FeCl_3$.

In the cyclic amide transition metal complex obtained in the manner described above, the covalence of the transition metal may be regulated if necessary by an oxidizing agent, or the counterion or axial ligand of the complex may be exchanged with another by a known method.

A bleaching catalyst containing the cyclic amide transition metal complex (1) in the present invention (referred to hereinafter as component (a)) has an excellent effect by blending it with a peroxy bleaching agent (referred to hereinafter as component (b)) selected from hydrogen peroxide, a peroxide or an organic peracid generating hydrogen peroxide in an aqueous solution.

The content of the component (a) in the bleaching composition of the invention containing the components (a) and (b) is preferably 0.0001 to 10% by weight, more preferably 0.0001 to 3% by weight. The content of the component (b) is preferably 0.01 to 99% by weight, more preferably 0.01 to 80% by weight. The ratio by weight of the component (b) to the component (a), that is, (b)/(a), is preferably 10 to 100,000, more preferably 10 to 50,000, from the viewpoint of the effective action of the component (a) as a bleaching catalyst to exhibit excellent bleaching performance.

The component (b) is preferably hydrogen peroxide or a peroxide generating hydrogen peroxide in an aqueous solution. The peroxide generating hydrogen peroxide in an aqueous solution includes sodium percarbonate, a sodium tripolyphosphate/hydrogen peroxide adduct, a sodium pyrophosphate/hydrogen peroxide adduct, a urea/hydrogen peroxide adduct, sodium perborate.$1H_2O$, sodium perborate.$4H_2O$, sodium peroxide and calcium peroxide, among which sodium percarbonate, sodium perborate.$1H_2O$ and sodium perborate.$4H_2O$ are preferable.

The bleaching composition of the present invention may be in a powdery or liquid form, and besides the essential ingredients described above, an alkali, a surfactant, a sequestering agent etc. can be contained. Preferable examples of the alkali include sodium carbonate, potassium carbonate etc. The surfactant is preferably an anionic surfactant or a nonionic surfactant, and the anionic surfactant includes sodium alkyl benzene sulfonate, sodium alkyl sulfate etc. having a C10 to C18 alkyl group, and the nonionic surfactant includes various polyoxyethylene alkyl ethers. The content of the surfactant in the bleaching composition of the present invention is preferably 50 wt % or less, more preferably 0.5 to 40 wt %.

The sequestering agent includes phosphate, phosphonocarboxylate, polyacrylate etc. The content of the sequestering agent in the bleaching composition of the present invention is preferably 30 wt % or less, more preferably 0.1 to 20 wt %, from the viewpoint of the bleaching effect.

A re-contamination inhibitor, a filler, an enzyme, a fluorescent brightener, a dye, a pigment, a perfume etc. can be added if necessary to the bleaching composition of the present invention.

The bleaching composition of the present invention can be added to a powdery or liquid detergent for cloth, a detergent for hard surface, a detergent for automatic dishwashers, a detergent for false teeth, etc., to confer bleach performance or an ability to prevent color migration. Further, the bleaching composition of the present invention can be used in various industrial applications such as hair bleach and bleach of wood pulp and salvaged paper.

The bleaching catalyst and bleaching composition of the present invention have a sufficient bleaching ability even at low temperatures of 30° C. or less and do not cause damage to fibers or bleach of dyes.

The bleaching catalyst and bleaching composition of the present invention have an excellent bleaching effect even at low temperatures and are excellent in an effect of preventing color migration in fibers with less bleach of dyes and less damage to fibers.

EXAMPLES

Production Example 1

A cyclic Fe complex represented by formula (I-a-1) (hereinafter, also referred to as cyclic Fe complex (I-a-1)) was synthesized according to the method in scheme 1.

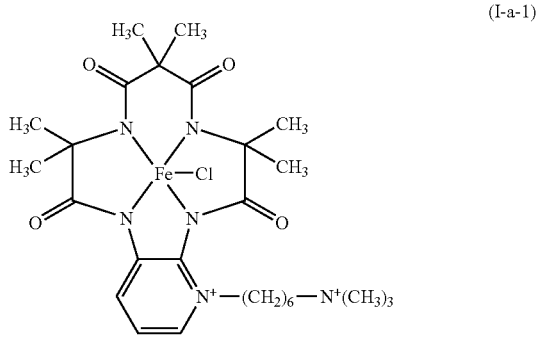

(I-a-1)

(a) Synthesis of Large Cyclic Tetramide (5-1)

4.5 g (14.9 mmol) macrolinker of the above formula (2) wherein $R^1$ to $R^6$ each represent a methyl group was dried at 100° C. for 2 hours under vacuum, and 130 ml anhydrous pyridine and 4.5 mL (36 mmol) pivaloyl chloride were added thereto and heated under reflux at 115° C. for 24 hours (conversion into oxazolone). 1.56 g (14.4 mmol) of 2,3-diaminopyridine was added thereto and heated for 3 days under reflux, and 15 mL deionized water was added thereto and stirred for 24 hours at 100° C. After the solvent was distilled away, a black viscous product was obtained. This viscous product was dissolved in a solution of 50 ml water/20 ml ethanol containing 3.6 g (34 mmol) $Na_2CO_3$, stirred for 30 minutes and adjusted to pH 9 with $Na_2CO_3$. The solvent was distilled away, 100 ml ethanol was added to the black viscous product, and precipitated inorganic salts were removed by filtration. The ethanol in the resulting filtrate was distilled away, whereby black solids were obtained. The solids were dispersed in acetonitrile, stirred for 13 hours and filtered to give a dark brown filtrate. To extract the whole of the desired product, this operation was repeated several times. The resulting filtrates were combined and the solvent was distilled away, whereby brown solids were obtained. The solids were triturated in petroleum ether, filtered and dried to give about 5 g brown powder.

The brown powder was dissolved in a mixed solvent of 25 ml ethanol and 100 ml water, and the solvent was gradually distilled away under heating, to precipitate black viscous insolubles. A filtrate obtained by removing the insolubles was concentrated to give about 3.2 g black viscous product. When 5 ml methanol was added thereto, white crystals were obtained. By recovery by filtration and subsequent drying, 530 mg (yield 9.5%) of the title compound of formula (5) wherein $R^1$ to $R^6$ each represent a methyl group was obtained in the form of white crystals.

Rf 0.28 (CH$_2$Cl$_2$/MeOH=95/5). IR (KBr, cm$^{-1}$): 3355, 3315 (NH), 2993, 2947 (CH), 1701, 1635 (C=O). $^1$H-NMR (δppm, DMSO): 1.42 (s, 6H), 1.44 (s, 6H), 1.46 (s, 6H), 7.28 (dd, 1H), 7.78 (s, 1H), 7.83 (s, 1H), 7.97 (d, 1H), 8.21 (d, 1H), 8.24 (s, 1H), 8.85 (s, 1H). $^{13}$C-NMR (δppm, DMSO): 22.02, 24.41, 25.19, 50.65, 57.59, 57.65, 121.96, 128.91, 132.64, 142.75, 144.41, 171.96, 172.82, 173.26, 173.58.

(b) Synthesis of Large Cyclic Tetramide (6-1) Modified With ω-Halogenoalkyl Pyridinium 1,6-Dibromohexane, 5 ml (32.5 mmol, 244 equivalents), was added to the large cyclic tetramide (5-1), 50 mg (0.133 mmol), obtained in (a), and the mixture was aged at 100° C. for 6 days while the reaction was monitored with TLC. The reaction product was purified by silica gel column chromatography, to give 54 mg (yield 66%) of the title compound of formula (6) wherein $R^1$ to $R^6$ each represent a methyl group, n is 6, and X is Br, was obtained in the form of white powder.

Rf 0.45 (CH$_2$Cl$_2$/MeOH=95/5). $^1$H-NMR (δppm, CDCl$_3$): 1.32 (m, 2H), 1.48 (m, 2H), 1.52 (s, 6H) 1.608 (s, 6H), 1.614 (s, 6H), 1.83 (m, 4H), 3.4 (t, 2H), 4.08 (t, 2H), 6.30 (s, 1H), 6.84 (dd, 1H), 7.33 (dd, 1H), 7.54 (s, 1H), 8.74 (dd, 1H), 9.22 (s, 1H). $^{13}$C-NMR (δppm, CDCl$_3$): 23.13, 25.71, 25.84, 27.62, 28.79, 32.30, 33.46, 50.54, 55.35, 58.45, 59.32, 114.96, 125.95, 131.87, 133.01, 151.67, 172.09, 173.66, 174.01, 175.99.

(c) Synthesis of Cyclic Fe Complex (I-a-1) Ligand

The large cyclic tetramide modified with ω-halogenoalkyl pyridinium (6-1), 47 mg (0.076 mmol), obtained in (b) was dissolved in 20 ml methanol, and then 100 μl (0.47 mmol, 8 equivalents) of 30% aqueous trimethylamine was added thereto and the mixture was aged at 60° C. While the reaction was monitored with TLC, the mixture was aged for 2 days during which 30% aqueous trimethylamine was added thereto whenever necessary (total: 56 equivalents). After the solvent was distilled away, the product was purified by re-crystallization from a dichloromethane/ethyl ether system to give the title compound, 47 mg (yield 92%), in the form of white powder.

IR (KBr, cm$^{-1}$): 2981, 2937 (CH), 1678 (C=O). $^1$H-NMR (δppm, D$_2$O): 1.21 (bs, 4H), 1.38 (s, 12H), 1.44 (s, 6H), 1.60 (t, 2H), 1.69 (t, 2H), 2.93 (s, 9H), 3.12 (t, 2H), 4.02 (t, 2H), 7.23 (dd, 1H), 8.01 (d, 1H), 8.33 (d, 1H) $^{13}$C-NMR (δppm, D$_2$O): 22.23, 25.21, 25.33, 28.77, 51.12, 52.87, 55.76, 58.44, 58.81, 66.54, 118.71, 130.83, 135.99, 137.97, 153.11, 173.81, 174.39, 176.34, 178.2.

(d) Synthesis of Cyclic Fe Complex (I-a-1)

38 mg (0.056 mmol) of the ligand obtained in (c) was dissolved in 10 mL anhydrous THF, then charged with 0.33 mL (6.0 equivalents) of a THF solution of 1.0 M bistrimethylsilylamide lithium at room temperature and aged for 10 minutes. Thereafter, the mixture was charged with 13.5 mg (about 1.5 equivalents) of FeCl$_3$ powder and stirred in a nitrogen atmosphere at room temperature for 4 hours. The resulting crystals were filtered and dried to give the title compound, 33.6 mg (yield 99%), in the form of dark yellow powder.

UV (in distilled water): λmax: 267 nm (ε=7424), 318 nm (ε=6725) IR (KBr, cm$^{-1}$): 1630 (amide C=O).

Production Example 2

A cyclic Fe complex represented by formula (I-b-1) (hereinafter, also referred to as cyclic Fe complex (I-b-1)) was synthesized according to the method in scheme 1.

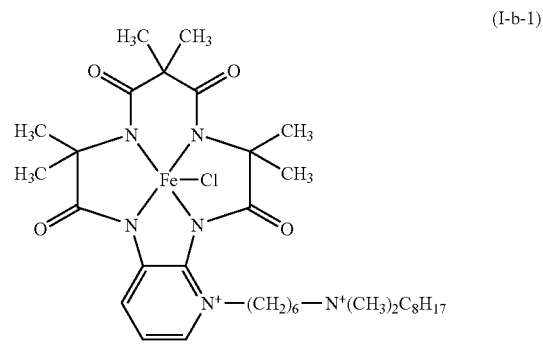

(I-b-1)

(a) Synthesis of Cyclic Fe Complex (I-b-1) Ligand

The large cyclic tetraamide modified with ω-halogenoalkyl pyridinium (6-1), 101 mg (0.164 mmol), obtained in (b) in Production Example 1 was dissolved in 10 ml isopropyl alcohol, and 337 μl (1.64 mmol, 10 equivalents) of N,N-dimethyloctylamine was added thereto, and the mixture was reacted at 70° C. for 69 hours. After the solvent was distilled away, the residues were washed with ethyl ether to remove an excess of N,N-dimethyloctylamine to give 135 mg (0.174 mmol, yield 106%) of the title compound in the form of white powder.

Rf 0.00 (MeOH only), 0.66 (2% aq. KNO$_3$/MeCN=1/1). $^1$H-NMR (δppm, D$_2$O): 0.696 (t, 3H), 1.109 (m, 6H), 1.182 (m, 8H), 1.375 (s, 12H), 1.441 (s, 6H), 1.548 (m, 4H), 1.681 (m, 2H), 2.854 (s, 6H), 3.071 (m, 4H), 4.013 (t, 2H), 7.228 (dd, 1H), 8.01 (d, 1H), 8.33 (d, 1H). IR (KBr, cm$^{-1}$): 2927, 2858 (CH), 1685, 1630 (amide C=O).

(b) Synthesis of Cyclic Fe Complex (I-b-1)

100.4 mg (0.1293 mmol) ligand obtained in (a) was dissolved (uniformly dissolved) in 10 mL anhydrous THF and then charged with 705 μL (6.0 equivalents) of a THF solution of 1.1 M bis(trimethylsilyl)amide lithium in a nitrogen stream at room temperature followed by aging for 30 minutes (pale yellow uniform solution). Thereafter, the solution was charged with 26.8 mg (about 1.5 equivalents) of FeCl$_2$ and stirred at room temperature for 21 hours in a nitrogen atmosphere at room temperature (dark brown solution with insolubles). For oxidizing Fe(II) into Fe(III), the solution was bubbled with oxygen for 2 hours. The crystals were recovered by filtration and then dissolved in methanol, and insolubles were removed by a membrane filter. The filtrate was concentrated and dried to give 175 mg dark brown viscous product. The resulting brown solids were subjected to gel filtration (elution with MeOH from Sephadex LH20), whereby low-molecular impurities were removed, and the eluate was concentrated and dried to give the title compound, 48 mg (yield 53%), in the form of dark brown solids.

UV (in distilled water): λmax: 269 nm (ε=9849), 316 nm (ε=9957) IR (KBr, cm$^{-1}$): 2927, 2858 (CH), 1630 (amide C=O)

Production Example 3

A cyclic Fe complex represented by formula (I-c-1) (hereinafter, also referred to as cyclic Fe complex (I-c-1)) was synthesized according to the method in scheme 1.

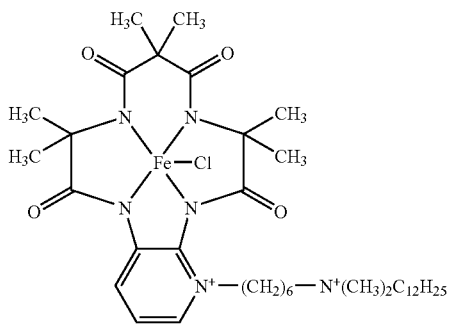

(I-c-1)

(a) Synthesis of Cyclic Fe Complex (I-c-1) Ligand 36 mg (0.058 mmol) of the large cyclic tetraamide modified with ω-halogenoalkyl pyridinium (6-1), obtained in (b) in Production Example 1, was dissolved in 15 ml isopropyl alcohol, and 319 μl (1.159 mmol, 20 equivalents) of N,N-dimethyldodecylamine was added thereto, and the mixture was reacted at 80° C. for 43 hours. After the solvent was distilled away, the residues were washed with ethyl ether to remove an excess of N,N-dimethyldodecylamine to give 47 mg (0.056 mmol, yield 96%) of the title compound in the form of white powder.

Rf 0.00 (MeOH only), 0.72 (2% aq. $KNO_3$/MeCN=1/1).

$^1$H-NMR (δppm, $D_2O$): 0.726 (t, 3H), 1.116 (m, 18H), 1.157 (m, 4H), 1.350 (s, 6H), 1.394 (s, 6H), 1.413 (s, 6H), 1.523 (m, 4H), 1.625 (m, 2H), 2.881 (m, 6H), 3.092 (m, 4H), 4.006 (m, 2H), 7.140 (dd, 1H), 7.958 (d, 1H), 8.36 (d, 1H).

IR (KBr, cm$^{-1}$): 2925, 2854 (CH), 1685, 1630 (amide C=O)

(b) Synthesis of Cyclic Fe Complex (I-c-1)

35.6 mg (0.0427 mmol) ligand obtained in (a) was dissolved (uniformly dissolved) in 7 mL anhydrous THF and then charged with 233 μL (6.0 equivalents) of a THF solution of 1.1 M bis(trimethylsilyl)amide lithium in a nitrogen stream at room temperature followed by aging for 10 minutes (pale yellow uniform solution). Thereafter, the solution was charged with a solution of 10.4 mg (about 1.5 equivalents) of $FeCl_3$ in 1 ml anhydrous THF and stirred at room temperature for 4 hours in a nitrogen atmosphere (dark brown solution with insolubles) The crystals were recovered by filtration and then dissolved in methanol, and insolubles were removed by a membrane filter. The filtrate was concentrated and dried to give 12.6 mg brown solid (yield 39%).

Rf 0.38 (2% aq. $KNO_3$/MeCN=1/1).

UV (in distilled water): λmax: 267 nm (ε=6389), 322 nm (ε=4843)

IR (KBr, cm$^{-1}$) 2927, 2856 (CH), 1630 (amide C=O)

Production Example 4

A cyclic Fe complex represented by formula (I-d-1) (hereinafter, also referred to as cyclic Fe complex (I-d-1)) was synthesized according to the method in scheme 1.

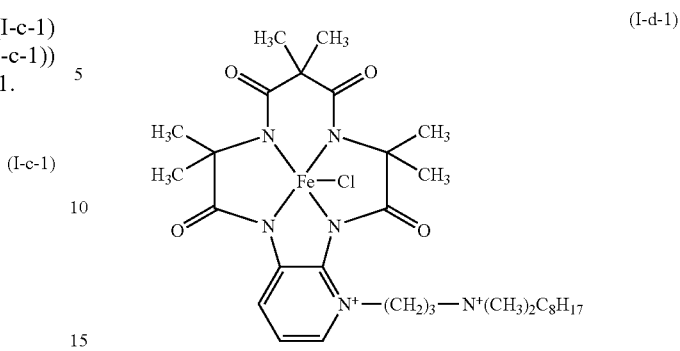

(I-d-1)

(a) Synthesis of Large Cyclic Tetraamide Modified With ω-Halogenoalkyl Pyridinium (6-2)

15 ml (148 mmol) 1,3-dibromopropane was added to the large cyclic tetraamide (5-1), 137 mg (0.365 mmol), obtained in (a) in Production Example 1, and while the reaction was monitored with TLC, the mixture was aged at 60° C. for 5 days. The reaction product was purified by silica gel column chromatography to give 98 mg (0.170 mmol, yield 47%) of the title compound of formula (6) wherein $R^1$ to $R^6$ each represent a methyl group, n is 3, and X is Br, was obtained in the form of white powder.

Rf 0.38 ($CH_2Cl_2$/MeOH=95/5). $^1$H-NMR (δppm, $CDCl_3$): 1.51 (s, 6H), 1.605 (s, 6H), 1.614 (s, 6H), 2.37 (m, 2H), 3.34 (t, 2H), 4.30 (t, 2H), 6.32 (s, 1H), 6.86 (dd, 1H), 7.41 (dd, 1H), 7.51 (s, 1H), 8.74 (dd, 1H), 9.19 (s, 1H). $^{13}$C-NMR (δppm, $CDCl_3$) 23.27, 25.88, 26.12, 29.79, 30.91, 50.77, 53.80, 58.66, 59.530, 115.31, 126.69, 132.68, 133.31, 151.89, 172.27, 173.90, 174.21, 176.40.

(b) Synthesis of Cyclic Fe Complex (I-d-1) Ligand

The large cyclic tetraamide modified with 77 mg (0.1334 mmol) of ω-halogenoalkyl pyridinium (6-2), obtained in (a), was dissolved in 9 ml of isopropyl alcohol and 274 μl (1.334 mmol, 10 equivalents) of N,N-dimethyloctylamine was added thereto. The mixture was reacted at 60° C. for 70 hours. After the solvent was distilled away, the residues were washed with ethyl ether to remove an excess of N,N-dimethyloctylamine to give white powder. The resulting colorless solids were purified by silica gel column chromatography (solvent: (1) MeOH→(2) 2% aq. $KNO_3$/MeCN=1/1). A purified product containing $KNO_3$ was dissolved in ethanol, and insolubles were removed as inorganic salts. As de-salting operation, gel filtration (elution with MeOH from Sephadex LH20) was conducted. 72 mg (0.0977 mmol, yield 73%) of the title compound was obtained in the form of white solids.

Rf 0.00 (MeOH only), 0.63 (2% aq. $KNO_3$/MeCN=1/1). $^1$H-NMR (δppm, $D_2O$): 0.695 (t, 3H), 1.12 (m, 10H), 1.366 (s, 6H), 1.387 (s, 6H), 1.434 (s, 6H), 1.46 (m, 2H), 2.201 (m, 2H), 2.894 (s, 6H), 3.10 (m, 2H), 3.16 (m, 2H), 4.10 (t, 2H), 7.25 (dd, 1H), 8.00 (dd, 1H), 8.39 (dd, 1H). IR (KBr, cm$^{-1}$): 2929, 2858 (CH), 1685, 1630 (amide C=O).

(c) Synthesis of Cyclic Fe Complex (I-d-1)

55.6 mg (0.0757 mmol) ligand obtained in (b) was dissolved (uniformly dissolved) in 5 ml anhydrous THF and then charged with 413 μL (6.0 equivalents) of a THF solution of 1.1 M bis(trimethylsilyl)amide lithium in a nitrogen stream at room temperature followed by aging for 5 minutes (yellowish brown→dark brown). Thereafter, the solution was charged with a solution of 18.4 mg (about 1.5 equivalents) of FeCl₃ in 1 ml anhydrous THF and stirred at room temperature for 4 hours in a nitrogen atmosphere (dark brown solution with insolubles) The crystals were recovered by filtration and then subjected to gel filtration (elution with MeOH from Sephadex LH20), whereby low-molecular impurities were removed, and the eluate was concentrated and dried to give the title compound, 30 mg (yield 60%), in the form of dark brown solids.

UV (in distilled water): λmax: 264 nm ($\epsilon$=12299), 336 nm ($\epsilon$=7054) IR (KBr, cm$^{-1}$): 2978, 2931, 2871 (CH), 1626 (amide C=O).

Examples 1 to 4 and Comparative Examples 1 to 2

The cyclic Fe complex (I-a-1) obtained in Production Example 1, the cyclic Fe complex (I-b-1) obtained in Production Example 2, the cyclic Fe complex (I-c-1) obtained in Production Example 3 and the cyclic Fe complex (I-d-1) obtained in Production Example 4 were used to measure bleaching performance by the following method. Bleaching performance was measured in the same manner by using a Fe-HM-DCB complex represented by formula (8) (complex described in WO9803625) as a comparative catalyst or without using any bleaching catalyst. The results are shown in Table 1.

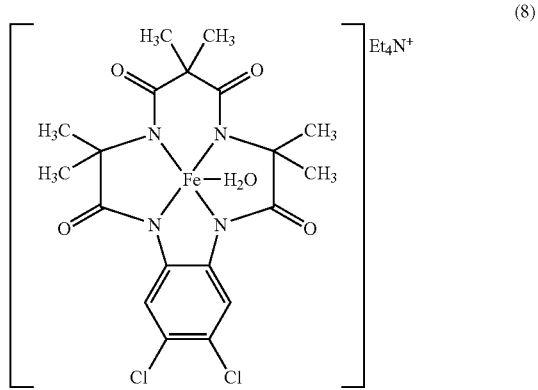

(8)

<Method 1 of Measuring Bleaching Performance>

(1) Preparation of a Dry Tea Extract Powder 10 g commercial tea leaves (Lipton) were extracted with 400 g hot water (90° C.) and then the tea leaves were freeze-dried. 2.53 g dark brown powder was obtained as dry tea extract powder.

(2) Measurement of Bleaching Performance

As a subject of bleaching, the dry tea extract powder was added at a concentration of 200 ppm to 10 ml of 0.05% aqueous sodium carbonate, and the bleaching catalyst was added at a concentration of 5 ppm and further 35% aqueous hydrogen peroxide was added at a concentration of 0.04% $H_2O_2$, to bleach the aqueous tea solution at 25° C. The aqueous tea solution before bleach (before addition of the aqueous hydrogen peroxide) and the aqueous solution after bleach treatment for 5 minutes were measured for their absorbance at 420 nm with a UV-VIS measuring instrument (HITACHI U-3300), and the degree of bleach was calculated according to the following equation:

Degree of bleach (%)=(1−absorbance after bleaching treatment/absorbance before bleaching treatment)×100

TABLE 1

| | Bleaching catalyst | Degree of bleach (%) |
|---|---|---|
| Example 1 | Cyclic Fe complex (I-a-1) in production example 1 | 85 |
| Example 2 | Cyclic Fe complex (I-b-1) in production example 2 | 86 |
| Example 3 | Cyclic Fe complex (I-c-1) in production example 3 | 84 |
| Example 4 | Cyclic Fe complex (I-d-1) in production example 4 | 80 |
| Comparative example 1 | Fe-HM-DCB complex of formula (8) | 71 |
| Comparative example 2 | Not added | 6 |

Examples 5 to 8 and Comparative Examples 3 to 4

The cyclic Fe complex (I-a-1) obtained in Production Example 1, the cyclic Fe complex (I-b-1) obtained in Production Example 2, the cyclic Fe complex (I-c-1) obtained in Production Example 3 and the cyclic Fe complex (I-d-1) obtained in Production Example 4 were used to measure bleaching performance by the following method. Bleaching performance was also measured in the same manner by using a Fe—HM-DCB complex represented by formula (8) (complex described in WO9803625) as a comparative catalyst or without using any bleaching catalyst. The results are shown in Table 2.

<Method 2 of Measuring Bleaching Performance>

(1) Preparation of a Cloth Stained With Tea 80 g Nitto Tea (yellow package) was boiled in 3 L deionized water for 15 minutes and filtered through a destarched, bleached cotton cloth. A cotton cloth was dipped in this solution, boiled therein for 15 minutes and then left for 2 hours. Then, the cloth was removed, air-dried and washed with water until the wash became uncolored, and then the cloth was dehydrated, pressed and subjected as a tea-stained cloth of 4×4 cm to an experiment.

(2) Measurement of Bleaching Performance

As a subject of bleaching, the tea-stained cloth prepared by the above method was dipped in 5 ml aqueous sodium carbonate (0.05%), and then 0.025 mg bleaching catalyst (solution concentration 5 ppm) and 35% aqueous hydrogen peroxide were added such that the concentration of $H_2O_2$ in the solution was 0.4%, and the stained cloth was subjected to bleaching treatment under the condition of 25° C./30 minutes. After bleaching treatment, the stained cloth was washed with water and dried, and the resulting stained cloth after bleaching and washing, the stained cloth before bleaching, and the original cotton cloth were measured for their reflectance at 460 nm with a UV-VIS measuring instrument (HITACHI U-3300), and the degree of bleach was determined according to the following formula:

Degree of bleach (%)=(reflectance after bleaching and washing−reflectance before bleaching)/(reflectance of the original cloth−reflectance before bleaching)×100

TABLE 2

| | Bleaching catalyst | Degree of bleach (%) |
|---|---|---|
| Example 5 | Cyclic Fe complex (I-a-1) in production example 1 | 59 |
| Example 6 | Cyclic Fe complex (I-b-1) in production example 2 | 47 |
| Example 7 | Cyclic Fe complex (I-c-1) in production example 3 | 45 |
| Example 8 | Cyclic Fe comples (I-d-1) in production example 4 | 40 |
| Comparative example 3 | Fe-HM-DCB complex of formula (8) | 27 |
| Comparative example 4 | Not added | 16 |

The invention claimed is:

1. A cyclic amide transition metal complex represented by formula (1)

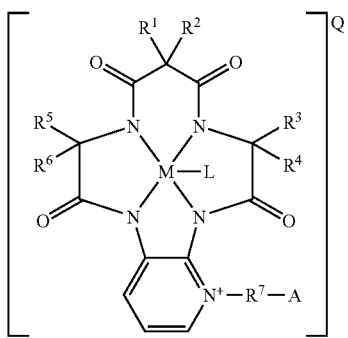

wherein $R^1$, $R^2$, $R^3$, $R^4$, $R^5$ and $R^6$ are the same or different and each represent a hydrogen atom, a C1 to C16 hydrocarbon, a perfluoroalkyl group or a halogen atom, $R^7$ represents an optionally substituted C1 to C18 alkylene or a perfluoroalkylene group, A represents a group having 1 to 3 quatemary ammonium groups substituted with a linear or branched alkyl group or linked with a linear or branched alkylene group, a cyclic quaternary ammonium group or a heterocyclic aromatic quaternary cation group which may be substituted with a linear or branched alkyl group, M represents a transition metal, L represents a ligand and Q represents an arbitrary counterion equilibrated stoichiometrically with a charge of the compound.

2. The cyclic amide transition metal complex according to claim 1, wherein in formula (1), $R^1$, $R^2$, $R^3$, $R^4$, $R^5$ and $R^6$ each represent a methyl group, $R^7$ represents a —($CH_2$)— group wherein n is an integer of 1 to 18, A represents —$N^+(CH_3)_2(C_mH_{2m+1})$ wherein m is an integer of 1 to 18, —$N^+(CH_3)_2$—($CH_2$)$_p$—$N^+(CH_3)_3$ wherein p is an integer of 1 to 18, or a pyridinium group, and M is Fe(III).

3. A bleaching catalyst comprising the cyclic amide transition metal complex according to claim 2.

4. A bleaching composition comprising (a) a bleaching catalyst comprising the cyclic amide transition metal complex according to claim 2 and (b) a peroxy bleaching agent selected from the group consisting of hydrogen peroxide and a peroxide or an organic peracid generating hydrogen peroxide in an aqueous solution thereof.

5. A bleaching composition comprising the cyclic amide transition metal complex according to claim 2 and one or more additional agents.

6. A bleaching catalyst comprising the cyclic amide transition metal complex according to claim 1.

7. A bleaching composition comprising (a) a bleaching catalyst comprising the cyclic amide transition metal complex according to claim 1 and (b) a peroxy bleaching agent selected from the group consisting of hydrogen peroxide and a peroxide or an organic peracid generating hydrogen peroxide in an aqueous solution thereof.

8. A bleaching composition comprising the cyclic amide transition metal complex according to claim 1 and one or more additional agents.

* * * * *